(12) United States Patent
Mao et al.

(10) Patent No.: US 7,834,145 B2
(45) Date of Patent: Nov. 16, 2010

(54) HCV PROTEASE SUBSTRATES

(75) Inventors: Shi-Shan Mao, North Wales, PA (US); S. Dale Lewis, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 646 days.

(21) Appl. No.: 11/886,149

(22) PCT Filed: Mar. 17, 2006

(86) PCT No.: PCT/US2006/009727

§ 371 (c)(1),
(2), (4) Date: Sep. 10, 2007

(87) PCT Pub. No.: WO2006/102087

PCT Pub. Date: Sep. 28, 2006

(65) Prior Publication Data

US 2009/0215101 A1 Aug. 27, 2009

Related U.S. Application Data

(60) Provisional application No. 60/664,152, filed on Mar. 22, 2005.

(51) Int. Cl.
*A61K 38/04* (2006.01)
*A61K 38/00* (2006.01)
*C07K 1/00* (2006.01)

(52) U.S. Cl. .................. 530/330; 530/323; 530/345

(58) Field of Classification Search .................. None
See application file for complete search history.

(56) References Cited

U.S. PATENT DOCUMENTS 5,739,002 A 4/1998 De Francesco et al.

FOREIGN PATENT DOCUMENTS

WO WO 97/08304 A2 3/1997

OTHER PUBLICATIONS

Makoto et al., 1993, "Proteolytic Processing and Membrane Association of Putative Nonstructural Proteins of Hepatitis C Virus" *Proc. Natl. Acad. Sci. USA* 90: 10773-10777.
Grakoui et al., 1993, "A Second Hepatitis C Virus-Encoded Proteinase" *Proc. Natl. Acad. Sci. USA* 90:10583-10587.
Gallinari et al., 1999, "Modulation of Hepatitis C Virus NS3 Protease and Helicase Activities Through the Interaction wtih NS4A" *Biochemistry* 38: 5620-5632.
Bianchi et al., 1996, "Synthetic Depsipeptide Substrates for the Assay of Human Hepatitis C Virus Protease" *Analytical Biochemistry* 237:239-244.
Taliani et al., 1996, "A Continuous Assay of Hepatitis C Virus Protease Based on Resonance Energy Transfer Depsipeptide Substrates" *Anayltical Biochemistry* 240:60-67.
Sperandio et al., 2002, "Highly Potent Non-peptidic Inhibitors of the HCV NS3/NS4A Serine Protease" *Bioorganic & Medeicinal Chemistry Letters* 12:3129-3133.
Attwood et al., 1999, "The Design and Synthesis of Potent Inhibitors of Hepatitis C Virus NS3-4A Proteinase" *Antivrial Chemistry & Chemotherapy*. 10:259-273.
Grakoui et al., 1993, "Expression and Identification of Hepatitis C Virus Polyprotein Cleavage Products" *Journal of Virology* 67:1385-1395.
Kakuichi et al., 1999, "A High Throughput Assay of the Hepatitis C Virus Nonstructural Protein 3 Serine Proteinase" *Journal of Virological Methods* 80:77-84.
Tomei et al., 1993, "NS3 Is a Serine Protease Required for Processing of Hepatitis C Virus Polyprotein" *Journal of Virology* 67:4017-4026.
Failla et al., 1994, "Both NS3 and NS4A Are Required for Proteolytic Procesing of Hepatitis C Virus Nonstructural Proteins" *Journal of Virology* 68:3753-3760.
Bartenschlager et al., 1993, "Nonstructural Protein 3 of the Hepatitis C Virus Encodes a Serine-Type Proteinase Required for Cleavage at the NS3/4 and NS4/5 Junctions" *Journal of Virology* 67:3835-3844.
Priestly et al., 2002, "P1 Phenethyl Peptide Boronic Acid Inhibitors of HCV NS3 Protease" *Bioorganic & Medicinal Chemistry Letters* 12:3199-32-3202.

*Primary Examiner*—Cecilia Tsang
*Assistant Examiner*—Thomas S Heard
(74) *Attorney, Agent, or Firm*—Melissa B. Wenk; Sheldon O. Heber

(57) ABSTRACT

The present invention features HCV NS3 protease substrates containing a europium label and a quenching group. The europium label and quenching group are located on different sides of an ester HCV NS3 protease cleavage site. The substrate can be used in a time-resolved fluorescence (TRF) assay to measure HCV protease activity.

6 Claims, 3 Drawing Sheets

HCV PROTEASE SUBSTRATES

RELATED APPLICATION DATA

This application is a §371 National Stage Application of PCT/US2006/009727, with an international filing date of Mar. 17, 2006, and claims the benefit of U.S. Provisional Application No. 60/664,152, filed Mar. 22, 2005.

BACKGROUND OF THE INVENTION

The references cited in the present application are not admitted to be prior art to the claimed invention.

Exposure to HCV results in an overt acute disease in a small percentage of cases, while in most instances the virus establishes a chronic infection causing liver inflammation and slowly progresses into liver failure and cirrhosis. (Iwarson, 1994. *FEMS Microbiol. Rev.* 14, 201-204.) Epidemiological surveys indicate HCV plays an important role in hepatocellular carcinoma pathogenesis. (Kew, 1994. *FEMS Microbiol. Rev.* 14, 211-220, Alter, 1995. *Blood* 85, 1681-1695.)

The HCV genome consists of a single strand RNA about 9.5 kb in length, encoding a precursor polyprotein about 3000 amino acids. (Choo et al., 1989. *Science* 244, 362-364, Choo et al., 1989. *Science* 244, 359-362, Takamizawa et al., 1991. *J. Virol.* 65, 1105-1113.) The HCV polyprotein contains the viral proteins in the order: C-E1-E2-p7-NS2-NS3-NS4A-NS4B-NS5A-NS5B.

Individual viral proteins are produced by proteolysis of the HCV polyprotein. Host cell proteases release the putative structural proteins C, E1, E2, and p7, and create the N-terminus of NS2 at amino acid 810. (Mizushima et al., 1994. *J. Virol.* 68, 2731-2734, Hijikata et al., 1993. *Proc. Natl. Acad. Sci. USA* 90, 10773-10777.)

The non-structural proteins NS3, NS4A, NS4B, NS5A and NS5B presumably form the virus replication machinery and are released from the polyprotein. A zinc-dependent protease associated with NS2 and the N-terminus of NS3 is responsible for cleavage between NS2 and NS3. (Grakoui et al., 1993. *J. Virol.* 67, 1385-1395, Hijikata et al., 1993. *Proc. Natl. Acad. Sci. USA* 90, 10773-10777.)

A distinct serine protease located in the N-terminal domain of NS3 is responsible for proteolytic cleavages at the NS3/NS4A, NS4A/NS4B, NS4B/NS5A and NS5A/NS5B junctions. (Barthenschlager et al., 1993. *J. Virol.* 67, 3835-3844, Grakoui et al., 1993. *Proc. Natl. Acad. Sci. USA* 90, 10583-10587, Tomei et al., 1993. *J. Virol.* 67, 4017-4026.) RNA stimulated NTPase and helicase activities are located in the C-terminal domain of NS3.

NS4A provides a cofactor for NS3 protease activity. (Failla et al., *J. Virol.* 1994. 68, 3753-3760, De Francesco et al., U.S. Pat. No. 5,739,002.) NS4A enhances NS-dependent cleavage at the different NS3 protease cleavage sites and is a required cofactor for cleavage at the NS3/4A and NS4B/NS5B junctions. (Gallinari et al., *Biochemistry* 38:5620-5632, 1999.) NS3 protease activity can be measured using peptides containing a region corresponding to a cleavage junction. (Steinkühler et al., International Publication WO 97/08304, published Mar. 6, 1997.) Peptides modified to contain an ester linkage at the NS3 cleavage site can also be used as a substrate to measure NS3 protease activity. (Steinkühler et al., International Publication WO 97/08304, published Mar. 6, 1997, Bianchi et al., *Analytical Biochemistry* 237:239-244, 1996.)

Different types of labels and assays have been employed to measure NS3 protease activity. Such assays include radiolabel assays, fluorometric assays, and fluorescence resonance energy transfer (FRET) assays. (Taliani et al., *Analytical Biochemistry* 240:60-67, 1996, Kakiuchi et al., *Journal of Virological Methods* 80:77-84, 1999, Gallinari et al., *Biochemistry* 38:5620-5632, 1999, Berdichevsky et al., *Journal of Virological Methods* 107:245-255, 2003.)

SUMMARY OF THE INVENTION

The present invention features HCV NS3 protease substrates containing a europium label and a quenching group. The europium label and quenching group are located on different sides of an ester HCV NS3 protease cleavage site. The substrate can be used in a time-resolved fluorescence (TRF) assay to measure HCV protease activity.

Thus, a first aspect of the present invention describes a HCV NS3 protease TRF substrate having the following structure:

$(B)_n\text{-}X^1\text{-}X^2\text{-}X^3\text{-}X^4\text{-}X^5\text{-}X^6\text{-}X^7\text{-}X^8\text{-}X^9\text{-}(Z)_m$     (SEQ ID NO:1)

wherein each B is an independently selected amino acid;
$X^1$ is either aspartic acid or glutamic acid;
$X^2$ is aspartic acid;
$X^3$ is methionine;
$X^4$ is glutamic acid;
$X^5$ is glutamic acid;
$X^6$ is 2-aminobutyric acid;
$X^7$ is alanine;
$X^8$ is serine;
$X^9$ is either lysine, histidine, cysteine or arginine;
each Z is an independently selected amino acid,
n is 0 to 10;
m is 0 to 10;
provided that $X^6$ is joined to $X^7$ by an ester linkage;
further provided that either: (a) at least one of a $(B)_n$ amino acid or $X^1$ is labeled with europium, and at least one of $X^9$ or an $(Z)_m$ amino acid is labeled with a quenching group; or (b) at least one of a $(B)_n$ amino acid or $X^1$ is labeled with a quenching group, and at least one of $X^9$ or an $(Z)_m$ amino acid is labeled with europium; and
further provided that the amino terminus amino acid is optionally modified with an amino terminus protecting group and the carboxyl terminus amino acid is optionally modified with a carboxyl terminus protecting group.

Another aspect of the present invention features a method of assaying HCV protease activity using a HCV NS3 protease TRF substrate. The substrate contains a europium label and a quencher on different sides of the NS3 protease cleavage site. Measuring europium signal production provides an indication of HCV protease activity.

The HCV NS3 protease assay involves NS3 protease, NS4A, the NS3 TRF substrate, and conditions where the NS3 is active. In a preferred embodiment, the assay is employed to measure the ability of a compound to affect NS3 protease activity.

Reference to open-ended terms such as "comprises" allows for additional elements or steps. Occasionally phrases such as "one or more" are used with or without open-ended terms to highlight the possibility of additional elements or steps.

Unless explicitly stated reference to terms such as "a" or "an" is not limited to one. For example, "a cell" does not exclude "cells". Occasionally phrases such as one or more are used to highlight the possible presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

The present invention features HCV NS3 protease TRF substrates. The substrate contains a europium label and quenching group located on different sides of an ester HCV NS3 protease cleavage site. In the absence of cleavage, the quenching group absorbs emission from the europium label. If the substrate is cleaved, europium signal production can be measured.

Figure 1:
FIG. 1 illustrates a TRF HCV NS3 protease assay. "Eu" refers to europium. "QSY" refers to a quenching group.
Figure 1:
Figure 1:
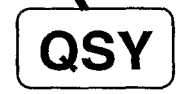
Figure 1:
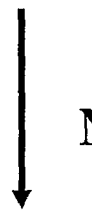
Figure 1:
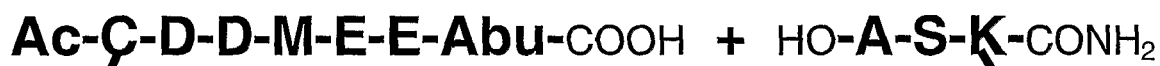
Figure 1:
Figure 1:
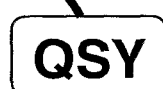

FIG. 1 illustrates the use of a europium labeled substrate to measure HCV NS3 protease activity. A one letter code is used to list amino acids in FIG. 1. Standard nomenclature for amino acids is: A=Ala=Alanine; C=Cys=Cysteine; D=Asp=Aspartic acid; E=Glu=Glutamic acid; F=Phe=Phenylalanine; G=Gly=Glycine; H=His=Histidine; I=Ile=Isoleucine; K=Lys=Lysine; L=Leu=Leucine; M=Met=Methionine; N=Asn=Asparagine; P=Pro=Proline; Q=Gln=Glutamine; R=Arg=Arginine; S=Ser=Serine; T=Thr=Threonine; V=Val=Valine; W=Trp=Tryptophan; and Y=Tyr-Tyrosine. "Abu" indicates aminobutyric acid.

Advantages of the europium labeled substrate include a good signal to noise ratio, high fluorescence, rapid cleavage by low concentration of HCV NS3 protease and high sensitivity. The high fluorescence signal enables the use of low substrate concentrations.

Low testing enzyme concentration is important for characterizing potent inhibitors, especially those with IC50<1 nM. As illustrated in the Examples, the europium labeled substrate was cleaved rapidly and efficiently by low concentrations of HCV NS3 protease.

High sensitivity facilitates high throughput screening using a multi-well format, such as a 3456-well format. Application of a 3456 format requires very small amounts of enzyme, substrate, and compounds.

HCV NS3 Protease Substrate

HCV NS3 protease substrates featured herein comprises, or consists, of the following structure $(B)_n-X^1-X^2-X^3-X^4-X^5-X^6-X^7-X^8-X^9-(Z)_m$ (SEQ ID NO:1)

wherein each B is an independently selected amino acid;
$X^1$ is either aspartic acid or glutamic acid; preferably aspartic acid;
$X^2$ is aspartic acid;
$X^3$ is methionine;
$X^4$ is glutamic acid;
$X^5$ is glutamic acid;
$X^6$ is 2-aminobutyric acid;
$X^7$ is alanine;
$X^8$ is serine;
$X^9$ is either lysine, histidine, cysteine or arginine; preferably lysine;
each Z is an independently selected amino acid;
n is 0 to 10; preferably 0 to 5; more preferably 1; more preferably cysteine,
m is 0 to 10; preferably 0 to 5; more preferably 0;
provided that $X^6$ is joined to $X^7$ by an ester linkage;
further provided that either: (a) at least one of a $(B)_n$ amino acid or $X^1$ is labeled with europium, and at least one of $X^9$ or an $(Z)_m$ amino acid is labeled with a quenching group; or (b) at least one of a $(B)_n$ amino acid or $X^1$ is labeled with a quenching group, and at least one of $X^9$ or an $(Z)_m$ amino acid is labeled with europium; and
further provided that the amino terminus amino acid is optionally modified with an amino terminus protecting group and the carboxyl terminus amino acid is optionally modified with a carboxyl terminus protecting group.

A protecting group at the N-terminal amino group reduces the reactivity of the amino terminus under in vivo conditions. Examples of amino protecting groups include acetyl, propel, succinyl, benzyl, benzyloxycarbonyl and t-butyloxycarbonyl.

A protecting group at the C-terminal carboxyl group reduces the reactivity of the carboxyl terminus under in vivo conditions. The carboxyl terminus protecting group is preferably attached to the a-carbonyl group of the last amino acid. Examples of carboxyl terminus protecting groups include amide, methylamide, and ethylamide.

Suitable quenching groups can quench fluorescence of europium around 615 nm. Examples of quenching group include QSY dyes (diarylrhodamine derivatives) such as QSY 7, QSY 9, QSY 21 (Molecular Probes); Dabcyl, blackhole quenching (BHQ); and Bodipyl.

Europium labeled peptides can be produced using techniques well known in the art, or commercially obtained. Europium labeled peptide can be obtained, for example, from Perkin-Elmer.

The europium label and quenching group should be about 8 to about 20 amino acids apart. Additional "B" and "Z" amino acids, if present, should be chosen to not adversely affect the ability of the substrate to be cleaved. Naturally occurring sequences around NS4A/4B cleavage site can be used to guide the addition of "B" and "Z" amino acids.

In different embodiments, any combination of substituents can be employed with any combination of one or more preferred or more preferred substituents. A preferred combination has the following structure:

(SEQ ID NO: 2)

Ac-Cys-Asp-Asp-Met-Glu-Glu-Abu-[COO]-Ala-Ser-Lys-NH$_2$
　　　　　　　　　　　　　　　　　|　　　　　　　　　　　　　　　|
　　　　　　　　　　　　　　　　 Eu　　　　　　　　　　　　　　　Q where Eu is europium, Q is the quenching group, and Ac is acetyl. Preferably, Q is QSY7:

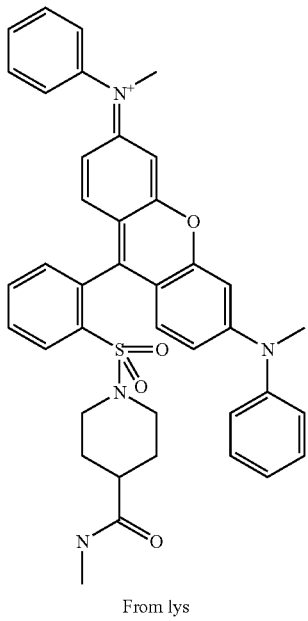

From lys

Techniques for chemical synthesis and labeling of polypeptides are well known in the art. Examples of such techniques are provided by Vincent, *Peptide and Protein Drug Delivery*, New York, N.Y., Decker, 1990, Bianchi et al., *Analytical Biochemistry* 237:239-244, 1996, Taliani et al., *Analytical Biochemistry* 240:60-67, 1996, and Steinkühler et al., International Publication WO 97/08304, published Mar. 6, 1997.

HCV NS3 Protease Assay

Measuring HCV NS3 protease activity has different uses, such as being used to study NS3 protease activity and to identify or evaluate HCV NS3 protease inhibitory compounds. HCV NS3 protease inhibitory compounds can be used to decrease replication of HCV.

Compounds inhibiting HCV replication have research and therapeutic applications. Research applications include the study of HCV replication. Therapeutic applications include using those compounds having appropriate pharmacological properties such as efficacy and lack of unacceptable toxicity to treat or inhibit onset of HCV in a patient.

HCV NS3 protease activity can be measured using the substrate described herein under conditions wherein NS3 is active. Such conditions include the use of NS4A and proper buffer conditions. Conditions compatible with NS3 activity, and methods for obtaining NS3 and N4A, are well known in the art. (De Francesco et al., U.S. Pat. No. 5,739,002, Steinkühler et al., International Publication WO 97/08304, published Mar. 6, 1997, Bianchi et al., *Analytical Biochemistry* 237: 239-244, 1996, Taliani et al., *Analytical Biochemistry* 240: 60-67, 1996, Kakiuchi et al., *Journal of Virological Methods* 80:77-84, 1999.)

EXAMPLES

Examples are provided below further illustrating different features of the present invention. The examples also illustrate useful methodology for practicing the invention. The examples do not limit the claimed invention.

Example 1

HCV NS3 Protease TRF Assay

An HCV NS3 protease assay was performed using the TRF substrate illustrated in FIG. 1 with QSY 7 as the quencher (Q). The unlabeled peptide was produced and sent to Perkin-Elmer. Perkin-Elmer added Europium and QSY-7.

HCV NS3 and NS4B were obtained using the techniques described in Gallinari et al., *Biochemistry* 38:5620-5632, 1999. NS3 was obtained from a HCV genotype 1b BK strain and a HCV genotype 2b strain isolated from a patient.

The TRF substrate (final 100 nM) was added to 100 µl of buffer with various concentrations of full length recombinant HCV NS3-NS4A. The assay buffer contained: 50 mM HEPES, pH 7.5, 150 mM NaCl, 15% glycerol, 0.15% Triton X-100, 10 mM DTT, and 0.1% PEG 8000. The reaction was quenched after 1 hour at room temperature with 100 µl of 500 mM MES, pH 5.5. For the continuous assay, the reaction mixture were reading for 30-120 minutes.

Figure 2:
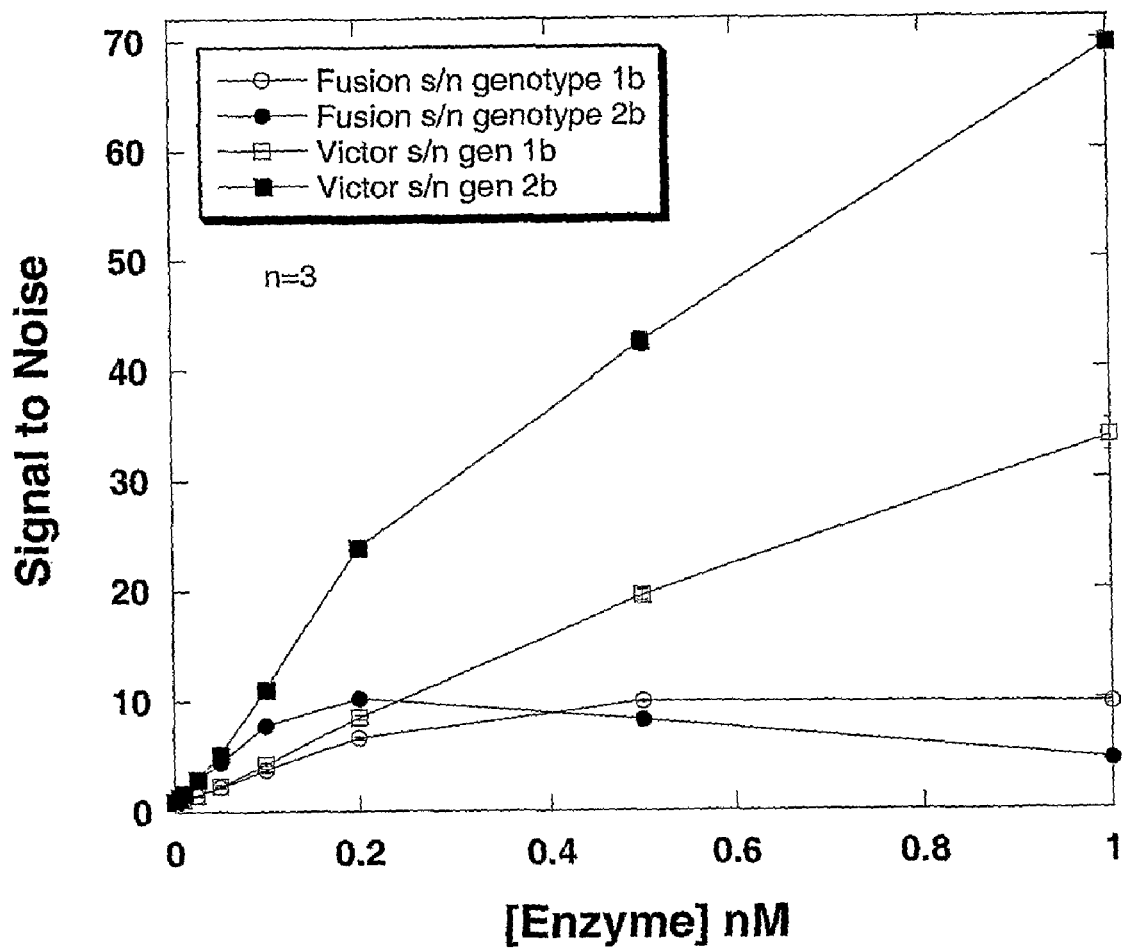
FIG. 2 illustrates results from an end-point TRF HCV NS3 protease assay. The assay employed 100 nM of TRF substrate and varying concerning of enzyme (NS3-NS4). Results are shown using a Perkin-Elmer Fusion machine and a Perkin-Elmer Victor machine.

Fluorescence was detected using either Fusion or Victor (Perkin Elmer instruments) with the following setting: EX 330 nm, EM 620 nm with 50-400 µs delay. The results are shown in FIG. 2.

The europium labeled NS3 substrate was hydrolyzed by NS3 and showed a signal to background ratio higher than 20. Europium shows high fluorescence signal, hence low concentrations of the substrate (<100 nM) can be used. The substrate was cleaved rapidly and efficiently by low concentrations (<0.1 nM) of HCV NS3-4A. Typical concentrations utilized in the available FRET assays are at least 10-fold higher. (Kakiuchi et al., *J. Virol. Method.*, 80:77-84, 1999.)

Low testing enzyme concentration is important for characterizing potent inhibitors, especially those with $IC_{50}$<1 nM. To measure the inhibition constants the concentrations of the protein should be below the compounds tested. The common practice requires inhibitor concentrations including the concentration below the inhibition constants.

When the testing inhibitor concentrations are close to the inhibition constant, so-called tight-binding inhibitors, a mathematic excise is used to obtain the actual inhibition constant. The accuracy of the inhibition constants depends highly on the quality of the experimental data.

When the inhibition constant is below the testing enzyme concentration, the results are only the titration of the active enzyme. For example, there is no difference in the inhibition constant using 50 nM enzyme with an inhibitor with $IC_{50}$ of either 1 nM or 0.01 nM. Both will be presented with an $IC_{50}$ of 25 nM, half of the enzyme concentration tested. Therefore it is important to employ the enzyme concentration much lower than the inhibition constants.

Several FRET substrates have been intensively used to determine NS3 protease activity. (Kakiuchi et al., *J. Virol. Method.*, 80:77-84, 1999, Spernadio et al., *Bioorg. Med. Chem. Lett.*, 12:3129-3133, 2002, Priestley et al., *Bioorg. Med. Chem. Lett.* 12:3199-3202, 2002, Attwood et al., *Antiviral Chem. Chemother.*, 10:259-273, 1999.) The enzyme concentrations are typically>1 nM with those substrates. In the described end-point TRF assay, compounds with less than 0.1 nM of NS3 with genotype 1b can be used. Hence it will be applicable to measure the inhibition constant as low as 1 nM.

Example 2

Continuous Assay

An HCV NS3 protease assay was performed using the TRF substrate illustrated in FIG. 1 with QSY 7 as the quencher (Q). HCV NS3 and NS4B were obtained using the techniques described in Gallinari et al., *Biochemistry* 38:5620-5632, 1999. NS3 was obtained from a HCV genotype 1b BK strain.

Figure 3:
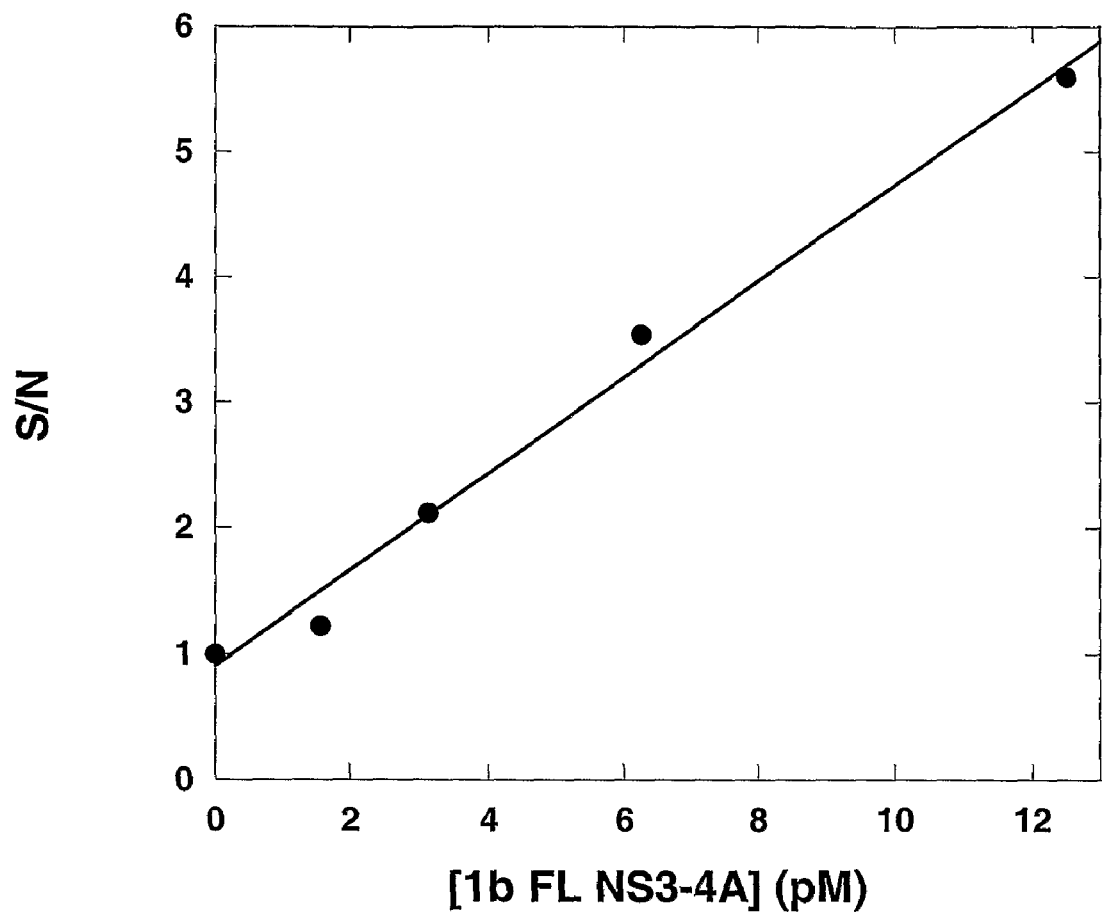
FIG. 3 illustrates enzyme titration with the continuous assay.

TRF measurement was initialed by adding the substrate (final 100 nM) to 100 µl of buffer with various concentrations of full length recombinant HCV NS3-NS4A. The assay buffer contained: 50 mM HEPES, pH 7.5, 150 mM NaCl, 15% glycerol, 0.15% Triton X-100, 10 mM DTT, and 0.1% PEG 8000. Fluorescence was detected continuously for 30-120 minutes using Fusion (Perkin-Elmer instruments) with the following setting: EX 330 nm, EM 620 nm with 50-400 µs delay. The results are shown in FIG. 3.

Other embodiments are within the following claims. While several embodiments have been shown and described, various modifications may be made without departing from the spirit and scope of the present invention.

What is claimed is:

1. A hepatitis C virus NS3 protease substrate comprising the following structure:

$$(B)_n-X^1-X^2-X^3-X^4-X^5-X^6-X^7-X^8-X^9-(Z)_m$$

(SEQ ID NO:1)
wherein each B is an independently selected amino acid;
$X^1$ is either aspartic acid or glutamic acid;
$X^2$ is aspartic acid;
$X^3$ is methionine;
$X^4$ is glutamic acid;
$X^5$ is glutamic acid;
$X^6$ is 2-aminobutyric acid;
$X^7$ is alanine;
$X^8$ is serine;
$X^9$ is either lysine, histidine, cysteine or arginine;
each Z is an independently selected amino acid;
n is 0 to 10;
m is 0 to 10;
provided that $X^6$ is joined to $X^7$ by an ester linkage;
further provided that either: (a) at least one of a $(B)_n$ amino acid or $X^1$ is labeled with europium, and at least one of $X^9$ or an $(Z)_m$ amino acid is labeled with a quenching group; or (b) at least one of a $(B)_n$ amino acid or $X^1$ is labeled with a quenching group, and at least one of $X^9$ or an $(Z)_m$ amino acid is labeled with europium; and further provided that the amino terminus amino acid is optionally modified with an amino terminus protecting group and the carboxyl terminus amino acid is optionally modified with a carboxyl terminus protecting group.

2. The substrate of claim 1, wherein said polypeptide consists of said structure and said quenching group is QSY7.

3. The substrate of claim 2, wherein n is 0 to 5, and m is 0 to 5.

4. The substrate of claim 3, wherein n is 1.

5. The substrate of claim 4, wherein said polypeptide consists of the following structure:

Ac-Cys-Asp-Asp-Met-Glu-Glu-Abu-[COO]-Ala-Ser-Lys-NH$_2$
         |                                              |
         Eu                                             Q (SEQ ID NO:2)
wherein Eu is europium, Q is said quenching group, and Ac is acetyl.

6. A method of assaying hepatitis C virus (HCV) protease activity comprising the steps of:
(a) combining together HCV NS3, HCV NS4A, and the substrate of claim 1, under conditions wherein said NS3 is active, and
(b) measuring europium signal production as an indication of HCV protease activity.

* * * * *

SEQUENCE LISTING

```
<160> NUMBER OF SEQ ID NOS: 3

<210> SEQ ID NO 1
<211> LENGTH: 29
<212> TYPE: PRT
<213> ORGANISM: Artificial Sequence
<220> FEATURE:
<223> OTHER INFORMATION: NS3 protease TRF substrate
<221> NAME/KEY: SITE
<222> LOCATION: (1)...(10)
<223> OTHER INFORMATION: Xaa = each individually either absent, Ala,
      Arg, Asn, Asp, Cys, Gln, Glu, Gly, His Ile, Leu, Lys,
      Met, Phe, Pro, Ser, Thr, Trp, Tyr, Val
<221> NAME/KEY: SITE
<222> LOCATION: (11)...(11)
<223> OTHER INFORMATION: Xaa = either Asp or Glu
<221> NAME/KEY: SITE
<222> LOCATION: (16)...(16)
<223> OTHER INFORMATION: Xaa = Abu
<221> NAME/KEY: SITE
<222> LOCATION: (16)...(17)
<223> OTHER INFORMATION: Xaa = ester linkage
<221> NAME/KEY: SITE
<222> LOCATION: (19)...(19)
<223> OTHER INFORMATION: Xaa = either Lys, His, Cys, or Arg
<221> NAME/KEY: SITE
<222> LOCATION: (20)...(29)
<223> OTHER INFORMATION: Xaa = each individually either absent, Ala,
      Arg, Asn, Asp, Cys, Gln, Glu, Gly, His Ile, Leu, Lys,
      Met, Phe, Pro, Ser, Thr, Trp, Tyr, Val

<400> SEQUENCE: 1

Xaa Xaa Xaa Xaa Xaa Xaa Xaa Xaa Xaa Xaa Xaa Asp Met Glu Glu Xaa
 1               5                   10                  15

Ala Ser Xaa Xaa Xaa Xaa Xaa Xaa Xaa Xaa Xaa Xaa Xaa
             20                  25

<210> SEQ ID NO 2
<211> LENGTH: 10
<212> TYPE: PRT
<213> ORGANISM: Artificial Sequence
<220> FEATURE:
<223> OTHER INFORMATION: NS3 protease TRF substrate
<221> NAME/KEY: ACETYLATION
<222> LOCATION: (1)...(1)
<221> NAME/KEY: SITE
<222> LOCATION: (1)...(1)
<223> OTHER INFORMATION: Xaa = Cys labeled with europium
<221> NAME/KEY: SITE
<222> LOCATION: (7)...(8)
<223> OTHER INFORMATION: Xaa = ester linkage
<221> NAME/KEY: SITE
<222> LOCATION: (10)...(10)
<223> OTHER INFORMATION: Xaa = Lys labeled with europium
<221> NAME/KEY: AMIDATION
<222> LOCATION: (10)...(10)
```

```
<400> SEQUENCE: 2

Xaa Asp Asp Met Glu Glu Xaa Ala Ser Xaa
 1               5                  10

<210> SEQ ID NO 3
<211> LENGTH: 7
<212> TYPE: PRT
<213> ORGANISM: Artificial Sequence
<220> FEATURE:
<223> OTHER INFORMATION: NS3 protease TRF substrate cleavage product
<221> NAME/KEY: ACETYLATION
<222> LOCATION: (1)...(1)
<221> NAME/KEY: SITE
<222> LOCATION: (1)...(1)
<223> OTHER INFORMATION: Xaa = Cys labeled with europium
<221> NAME/KEY: SITE
<222> LOCATION: (7)...(7)
<223> OTHER INFORMATION: Xaa = Abu

<400> SEQUENCE: 3

Xaa Asp Asp Met Glu Glu Xaa
 1               5
```